Aug. 11, 1964 H. C. SWIM ET AL Plant Pat. 2,436
ROSE PLANT
Filed Sept. 26, 1963
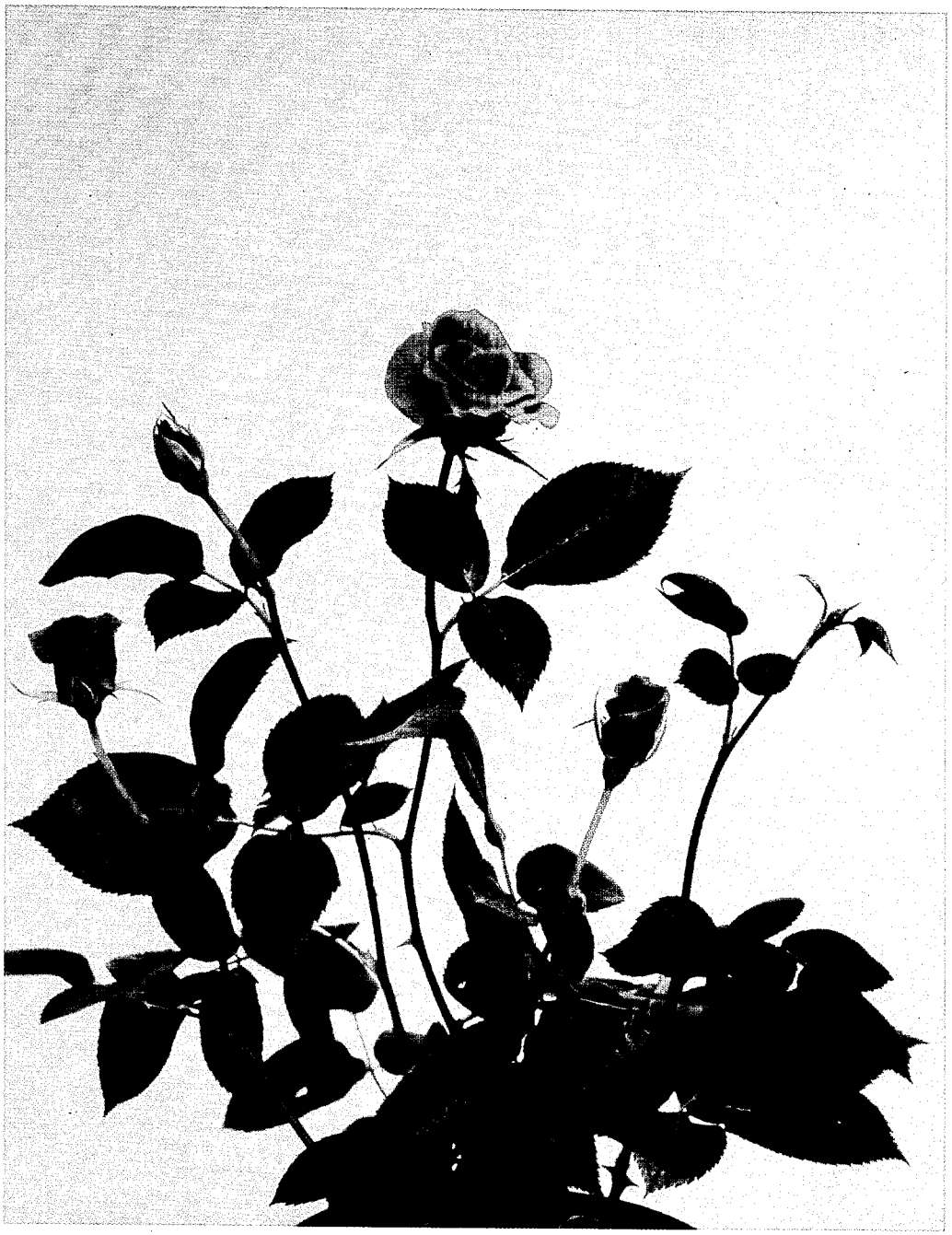
Inventors.
H. C. Swim and
O. L. Weeks
By: Robb & Robb
Attorneys.

United States Patent Office

Plant Pat. 2,436
Patented Aug. 11, 1964

2,436
ROSE PLANT

Herbert C. Swim, 1329 College Way, Ontario, Calif., and O. L. Weeks, 4759 Philadelphia, Chino, Calif.

Filed Sept. 26, 1963, Ser. No. 311,929
1 Claim. (Cl. Plt.—29)

The present invention relates to a new and distinct variety of rose plant of the floribunda class, which was originated by us by crossing the variety "Spartan" (Plant Patent No. 1,357) with the variety "Garnette" (unpatented).

As the result of this breeding, we have produced a new rose variety which is endowed with the following unique combination of characteristics which are outstanding therein and which distinguish it from its parents, as well as from all other varieties of which we are aware:

(1) A very vigorous habit of plant growth;

(2) Large dark green foliage of heavy, leathery texture;

(3) Relatively straight flower stems of good length, with consequent suitability for the florist trade;

(4) Prolific flower production;

(5) A flower bud form ranging from long-pointed to urn-shaped;

(6) Good flower petalage and double form of the flowers, with the petalage usually ranging from 25 to 35 petals when grown under greenhouse conditions in southern California; and (7) A distinctive and attractive general color tonality of the flowers from bud to the fully open stage, with the coloration being popularly described as ranging from Dark Red to Dark Purplish Red, with brighter pencil line margins on the petals.

In comparison with its seed parent "Spartan," the foliage of our new variety is darker green in color; the prickles have a substantially shorter base and longer length; the buds are long-pointed and urn-shaped, with no flatness at the tip, as distinguished from the short-pointed buds with tendency to flatness at the tip in the case of this parent; the Dark Red to Dark Purplish Red flowers of the new variety are distinctly different from the Orange-Red to Reddish Coral flowers of "Spartan"; and the flowers of the new variety have little or no fragrance, as distinguished from the very fragrant flowers of "Spartan."

As compared with its pollen parent "Garnette," the new variety has straighter stems, and the stems are of substantially greater length, as distinguished from the exaggerated zig-zag pattern from node to node in the case of the stem of "Garnette"; the leaves average substantially larger in size than those of this parent; the flower buds are longer pointed and more urn-shaped than the short-pointed flowers of "Garnette"; and the margins of the flower petals have a line of distinctly lighter and brighter red color than the adjacent areas, as distinguished from the lack of any visible contrast between the color of the margin of the petals and the adjacent areas in the flowers of "Garnette."

Asexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Bush; greenhouse; seedling; for cut flowers.
Class: Floribunda.
Breeding: Seedling.
*Seed parent.*—"Spartan."
*Pollen parent.*—"Garnette."
Propagation: Holds its distinguishing characteristics through succeeding propagations by budding.

*Flower*

Locality where grown and observed: Los Angeles, California.
Flowers borne: Both singly and several to stem; in irregular rounded clusters; on long stems of a strength varying from normal to strong.
Quantity of bloom: Abundant, in greenhouse.
Continuity: Continuous, more or less.
Fragrance: From slight to none.
Bud:
*Peduncle.*—From short to medium length; medium heavy caliper; erect; almost smooth; with few hairs or very small prickles, but with upper portion entirely smooth. Color—yellowish green.
*Before calyx breaks.*—Size—from medium to small for its class. Form—short; pointed with slight neck; with foliaceous appendages on the surface of the bud; with some occasional pinnate usually slender foliaceous parts extending beyond the tip of the bud equal to ¼ or more of its length. Color—between black and Dark Red, Plate 2.5R 3/7.
*As calyx breaks.*—Color—near Dark Red, Plate 2.5R 3/7.
*As first petal opens.*—Size—from small to medium for its class. Form—from long pointed to urn-shaped. Color: outside—near Dark Red, Plate 2.5R 3/7, with small area of greenish white about point of attachment; inside— principally Dark Red, Plate 2.5R 3/7 with line of near Moderate Red, Plate 2.5R 4/10 at margin, and with small area of greenish yellow about point of attachment; occasionally vegetative streaks of greenish white extend from the base and fan out progressively toward apex.
*Opening.*—Opens up well.
Bloom:
*Size (when fully open).*—From small to medium for its class; from 2¼ inches to 2½ inches.
*Petalage.*—Double; from 25 to 35 petals, plus 2 or 3 petaloids; arranged regularly.
*Form.*—From flat to high-centered; petals being slightly rolled outward, with outer petals rolling more conspicuously along upper portion of lateral margins and making apex an acute point.
Petals:
*Texture.*—Thick; leathery.
*Appearance.*—Inside—velvety. Outside—satiny.
*Shape.*—Outside—broadly orbicular, and scalloped with two shallow notches. Intermediate—nearly round, with apex usually entire and rounded when flattened, but with apex acute in naturally opened flower due to rolled upper margins. Inside—obovate, with apex made acute by folded down margins.

This description of a newly opened flower was made from a rose grown in a greenhouse during the month of June at Los Angeles, California:

*Color.*—Outer petal: outside surface — basically Moderate Red, Plate 2.5R 4/10, overlaid slightly and somewhat unevenly with Dark Red, Plate 2.5R 3/7, and with small area of greenish white at point of attachment; inside surface—basically near Moderate Red, Plate 2.5R 4/10, but overlaid heavily in center of petal with from Dark Red, Plate 2.5R 3/7 to black, and border at outer margins being without overlay, but with small area of greenish white at base which fans out in streaks toward apex in one or two petals. Intermediate petal: outside surface—near Deep Purplish Red, Plate 10RP 3/10, with small area of greenish white at base; inside surface—basically near Moderate Red, Plate 2.5R 4/10, with small area of greenish yellow at base, and all but a small border of the remainder of the petal being overlaid with from Dark Red, Plate 2.5R 3/7 to black in the areas between the veins. Inner petal: outside surface—near Deep Purplish Red, Plate 10RP 3/10, with small area of greenish white at base; inside surface—basically near Moderate Red, Plate 2.5R 4/10, overlaid with Dark Red, Plate 2.5R 3/7 and black in the areas between the veins, except at margin and at base, with base being near greenish white.

This description was made from a rose that was open for three days in a greenhouse during the month of June at Los Angeles, California:

*Color.*—Outer petal: outside surface—near Deep Purplish Red, Plate 10RP 3/10, with small area of greenish white at base; inside surface—basically varies from near Strong Red, Plate 5R 4/12 near base to near Strong Purplish Red, Plate 10RP 4/12 over upper half of petal, with the areas between veins over upper half of petal being heavily marked with Dark Purplish Red, Plate 10RP 3/10, and with small area of greenish white at base. Inner petal: outside surface—near Strong Purplish Red, Plate 10RP 4/12, with small area of greenish white at base; inside surface—basically near Strong Purplish Red, Plate 10RP 4/12, with the areas between the veins overlaid with Dark Red, Plate 2.5R 3/7, but with these colors mixed smoothly at margin, and with small area of greenish white at base.

*General color effect.*—Newly opened flower—near Dark Red, Plate 2.5R 3/7, with petal margins near Strong Red, Plate 5R 4/12. Three-days open—between Moderate Red, Plate 2.5R 4/10 and Strong Red, Plate 5R 4/12 at center of flower, with outer portion of flower near Deep Purplish Red, Plate 10RP 3/10.

*Behavior.*—Most drop off cleanly; petaloids sometimes persist for a few days.

*Flower longevity.*—On bush in garden—5 days in June. Cut roses grown in greenhouse and kept at living-room temperatures—6 days in June.

*Reproductive Organs*

Stamens: Many; arranged regularly about pistils and occasionally mixed with petaloids.

Filaments: From short to medium length; nearly all with anthers. Color—white, with light purplish central area.

Anthers: Very small; all open at once. Color—white, with yellow margins.

Pollen: Moderately abundant. Color—gold.

Pistils: Medium quantity.

Styles: Fairly even; short; medium caliper; tightly bunched.

Stigma: Color—whitish yellow.

Ovaries: Mostly enclosed in, but some protruding from, calyx.

Hips: From globular to vase-shaped; with inconspicuous neck; very smooth; walls thin and fleshy. Color—from orange russet to reddish at maturity.

Sepals: More or less permanent; moderately short; generally straight.

Seeds: From few to many; small.

*Plant*

Foliage:

*Leaves.*—Compound of 3–5 leaflets; moderately abundant; large size; moderately heavy; leathery.

*Leaflets.*—Shape—ovoid. Apex—from acute to acuminate. Base—round. Margin—simply serrate.

*Color.*—Mature: upper surface—very dark green; under surface—dark grey-green. Young: upper surface—reddish purple; under surface—lighter reddish purple.

*Rachis (the supporting stem of the compound leaf).*—Medium weight. Upper side—grooved; ridges with some stipitate glands. Under side—sparsely prickly.

*Stipules.*—Short; very narrow; with short points turning out at an angle of from 45° to 90°.

*Disease resistance.*—Good resistance to powdery mildew, as determined by comparison with other commercial rose varieties grown under comparable greenhouse conditions at Los Angeles, California.

Growth:

*Habit.*—Tall; bushy; upright-spreading.

*Growth.*—Very vigorous.

*Canes.*—From medium to heavy caliper.

*Main stems.*—Color—grey-green. Large prickles—few; medium length; straight; with short, broad base; color—brown. Small prickles—very few; color—brown. Hairs—none.

*Branches.*—Color—green. Large prickles—few; medium length; straight; with short, broad base; color—brown. Small prickles—very few; color—brown. Hairs—none.

*New shoots.* — Color — reddish purple. Large prickles—few; medium length; straight; with short, broad base; color — reddish purple. Small prickles — very few; color — reddish purple. Hairs—none.

We claim:

A new and distinct variety of rose plant of the floribunda class, substantially as herein shown and described, characterized particularly as to novelty by the unique combination of a very vigorous habit of plant growth, large dark green foliage of heavy and leathery texture, relatively straight flower stems of good length, good flower production, flower buds of long-pointed to urn-shaped form, good flower petalage and double form of the flowers, and a distinctive and attractive general color tonality of the flowers from the bud to the fully open stage corresponding from Dark Red to Dark Purplish Red, with brighter pencil line margins about the petals.

No references cited.